(12) United States Patent
Chang et al.

(10) Patent No.: US 8,700,135 B2
(45) Date of Patent: Apr. 15, 2014

(54) OPTICAL FIBER ARRAY PROBE IMAGING SYSTEM INTEGRATED WITH ENDOSCOPE

(71) Applicant: Korea Basic Science Institute, Daejeon (KR)

(72) Inventors: Ki Soo Chang, Daejeon (KR); Seon Young Ryu, Chungcheongbuk-do (KR); Sun Cheol Yang, Daejeon (KR); Geon Hee Kim, Daejeon (KR); Hae Young Choi, Chungcheongbuk-do (KR)

(73) Assignee: Korea Basic Science Institute, Daejeon (KR)

( * ) Notice: Subject to any disclaimer, the term of this patent is extended or adjusted under 35 U.S.C. 154(b) by 0 days.

(21) Appl. No.: 13/708,329

(22) Filed: Dec. 7, 2012

(65) Prior Publication Data
US 2013/0150731 A1    Jun. 13, 2013

(30) Foreign Application Priority Data

Dec. 12, 2011    (KR) .................. 10-2011-0132644

(51) Int. Cl.
*A61B 6/00* (2006.01)

(52) U.S. Cl.
USPC .................................. 600/478; 600/476

(58) Field of Classification Search
USPC .................. 600/160–182, 473–480
See application file for complete search history.

(56) References Cited

U.S. PATENT DOCUMENTS

| 4,987,884 | A  * | 1/1991 | Nishioka et al. | 600/181 |
| 6,547,722 | B1 * | 4/2003 | Higuma et al. | 600/133 |
| 6,767,322 | B1 * | 7/2004 | Futatsugi et al. | 600/133 |
| 7,805,034 | B2 * | 9/2010 | Kato et al. | 385/31 |
| 2004/0160682 | A1 * | 8/2004 | Miyano | 359/784 |
| 2006/0171025 | A1 * | 8/2006 | Quake et al. | 359/368 |

* cited by examiner

*Primary Examiner* — Sanjay Cattungal
(74) *Attorney, Agent, or Firm* — The Webb Law Firm'

(57) ABSTRACT

Provided is an imaging system which includes an optical fiber array probe unit integrated with an endoscope unit, thereby simultaneously measuring structural information and functional information of a sample. The optical fiber array probe unit includes an optical fiber array probe integrated with lenses including an optical fiber lens with a lens surface of a predetermined radius of curvature in which one ends of optical fibers are integrally connected with each other by heating a predetermined region including the one ends of two of the optical fibers using a heating means, as an optical fiber array probe integrated lens on which the light transmitted from the light source is incident and which guides light reflected from the sample, and a detector for selectively detecting the light transmitted from the optical fiber array probe integrated with lenses in a predetermined range of wavelength.

5 Claims, 4 Drawing Sheets

OPTICAL FIBER ARRAY PROBE IMAGING SYSTEM INTEGRATED WITH ENDOSCOPE

CROSS-REFERENCE TO RELATED APPLICATION

This application claims priority to and the benefit of Korean Patent Application No. 2011-0132644, filed on Dec. 12, 2011, the disclosure of which is incorporated herein by reference in its entirety.

BACKGROUND

1. Field of the Invention

The present invention relates to an imaging system, and more particularly, to an imaging system which includes an optical fiber array probe, in which an optical fiber lens is formed at one end of two strands of an optical fiber array, integrated with an endoscope, thereby achieving a compact imaging system with high ease of use.

2. Discussion of Related Art

An endoscope has been known as an in-vivo imaging system. The endoscope is composed of a long tube suitable for being inserted into a body of a human or animal, and a lens positioned in a distant tip of the endoscope is frequently used for providing images of internal areas of the body, that is, images of internal organs such as the stomach or intestines. Surgeons or other users of the endoscope may transmit the images to the outside of the body using an optical fiber cable connected with the endoscope.

In an imaging system that examines patients using such an endoscope, provided images provide only structural information about surfaces of organs, and therefore it is difficult to provide a large amount of biochemical information used for diagnosing lesions of the patient by a doctor.

Accordingly, there are many cases in which the doctor cuts a part of a tissue for accurate diagnosis, and then performs a complex process using separate measuring equipment to thereby diagnose the lesions. However, in such a biopsy process, there is a time-consuming problem to find the lesions through a complex process using separate equipment in order to extract biochemical information, in addition to inconvenience of having to cut the tissue.

Accordingly, there is a limitation on rapid and accurate diagnosis of lesions using only a simple endoscope system. Thus, there is a demand for a new technology for providing functional information in a variety of ways as well as structural information of the lesions.

Meanwhile, research on an imaging system using an optical fiber, for example, a fluorescence spectroscopy system, a fluorescence imaging system, or a nonlinear imaging system, has been conducted. These systems provide biochemical information of lesions in addition to structural information thereof, and thereby are able to be utilized as a means for early diagnosis of diseases. In order to utilize these systems as medical equipment for in-vivo diagnosis, the manufacture of a sample arm probe is necessary. The simplest method for manufacturing the sample arm probe is to simultaneously transmit an excitation beam and fluorescence signals or nonlinear signals using a single strand of optical fiber.

FIG. 1 is a schematic view showing an imaging system using a single strand of optical fiber. In such a structure, in order to separate excitation light and fluorescence signals or nonlinear signals generated from a sample to be transmitted and received, an optical splitter in a bulk form and lenses are needed, and this may cause difficulty in optical alignment when configuring the imaging system and complexity of the imaging system.

In order to solve these problems, optical fiber probes with a variety of structures have been developed. In the case of the fluorescence spectroscopy system, a method of separately using optical fiber for transmission of an excitation beam and detection of a fluorescence beam has been proposed. In the methods proposed in the related art, ends of two strands of optical fiber attached side-by-side to each other are used which are simply cut or polished at a predetermined angle.

However, in the case of cutting and using the end of the optical fiber, while the manufacture of the optical fiber probe is simple, the optical fiber is available only in a sample having significantly strong fluorescence signals due to significantly low coupling efficiency of fluorescence signals generated in the sample. In addition, in the case of polishing the end of the optical fiber at the predetermined angle, while improvement in the coupling efficiency of approximately 2 times may be achieved compared to the case of cutting and using the end of the optical fiber, two optical fibers have to be cut at an accurate angle, and therefore the manufacturing process becomes complex. Therefore, there is a demand for a new probe manufacturing method.

SUMMARY OF THE INVENTION

The present invention is directed to an imaging system in a new method, which may include an optical fiber array probe integrated with an endoscope.

The present invention is also directed to an imaging system which may include an optical fiber array probe system, in which an optical fiber lens is formed at one end of two strands of an optical fiber array, integrated with an endoscope, thereby simultaneously obtaining structural information and functional information of a sample.

The present invention is also directed to an imaging system which may check fluorescence signals or nonlinear signals of abnormal parts using an optical fiber array probe system immediately upon detecting any abnormality using an endoscope in examining interior parts of a human body.

According to an aspect of the present invention, there is provided an optical fiber array probe imaging system integrated with an endoscope, including: an endoscope unit; and an optical fiber array probe unit integrated with lenses, wherein the endoscope unit includes a light source, an endoscope probe through which the light source is transmitted to a sample, and a detection unit for detecting light reflected from the endoscope probe, and wherein the optical fiber array probe unit integrated with lenses includes an optical fiber array probe integrated with lenses including an optical fiber lens with a lens surface of a predetermined radius of curvature in which one ends of optical fibers are integrally connected with each other by heating a predetermined region including the one ends of two of the optical fibers using a heating means, as an optical fiber array probe integrated lens on which the light transmitted from the light source is incident and which guides light reflected from the sample, and a detector for selectively detecting the light transmitted from the optical fiber array probe integrated with lenses in a predetermined range of wavelength.

Preferably, the detector may include a filter for allowing a wavelength to be selectively passed.

In addition, a system control and display unit for controlling the system and displaying the detected light may be connected to the detector.

In addition, the optical fiber array probe integrated with lenses may be configured so as to be two-dimensionally or three-dimensionally scanned.

The imaging system may be manufactured as a fluorescence spectroscopy system, a fluorescence imaging system, or a system for measuring and analyzing nonlinear images.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
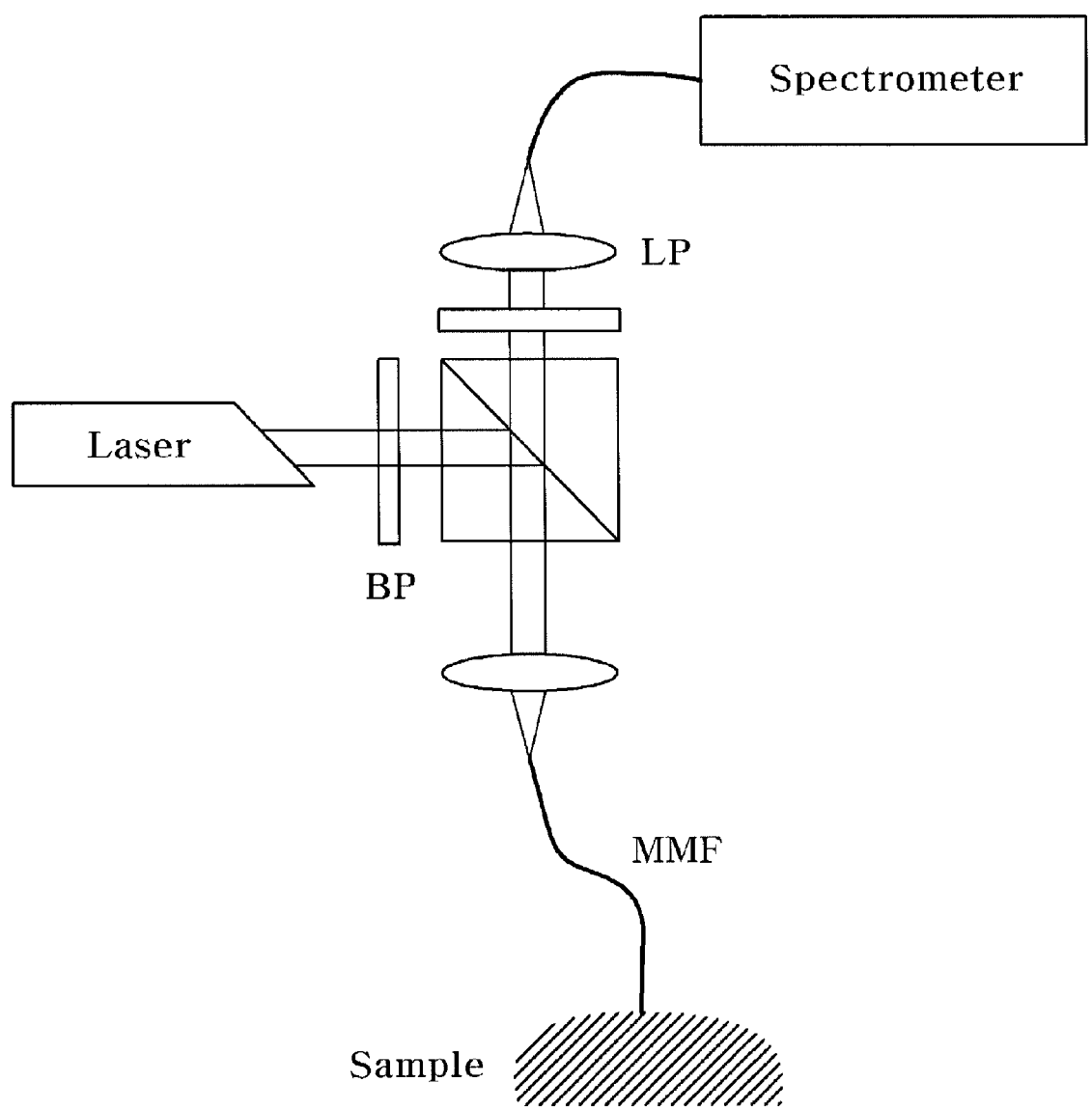
FIG. 1 is a schematic diagram showing an imaging system using a single strand of optical fiber.

Example embodiments of the present invention are described below in sufficient detail to enable those of ordinary skill in the art to embody and practice the present invention. It is important to understand that the present invention may be embodied in many alternate forms and should not be construed as limited to the example embodiments set forth herein.

Accordingly, while the invention can be modified in various ways and take on various alternative forms, specific embodiments thereof are shown in the drawings and described in detail below as examples. There is no intent to limit the invention to the particular forms disclosed. On the contrary, the invention is to cover all modifications, equivalents, and alternatives falling within the spirit and scope of the appended claims. Elements of the example embodiments are consistently denoted by the same reference numerals throughout the drawings and detailed description.

It will be understood that, although the terms first, second, A, B, etc. may be used herein in reference to elements of the invention, such elements should not be construed as limited by these terms. For example, a first element could be termed a second element, and a second element could be termed a first element, without departing from the scope of the present invention. Herein, the term "and/or" includes any and all combinations of one or more referents.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements. Other words used to describe relationships between elements should be interpreted in a like fashion (i.e., "between" versus "directly between," "adjacent" versus "directly adjacent," etc.).

The terminology used herein to describe embodiments of the invention is not intended to limit the scope of the invention. The articles "a," "an," and "the" are singular in that they have a single referent, however the use of the singular form in the present document should not preclude the presence of more than one referent. In other words, elements of the invention referred to in the singular may number one or more, unless the context clearly indicates otherwise. It will be further understood that the terms "comprises," "comprising," "includes," and/or "including," when used herein, specify the presence of stated features, items, steps, operations, elements, and/or components, but do not preclude the presence or addition of one or more other features, items, steps, operations, elements, components, and/or groups thereof Unless otherwise defined, all terms (including technical and scientific terms) used herein are to be interpreted as is customary in the art to which this invention belongs. It will be further understood that terms in common usage should also be interpreted as is customary in the relevant art and not in an idealized or overly formal sense unless expressly so defined herein.

Hereinafter, a preferable embodiment of the present invention will be described referring to accompanying drawings in detail. Throughout the accompanying drawings, the same reference numerals are used to designate the same or similar components, and redundant descriptions thereof are omitted.

Figure 2:
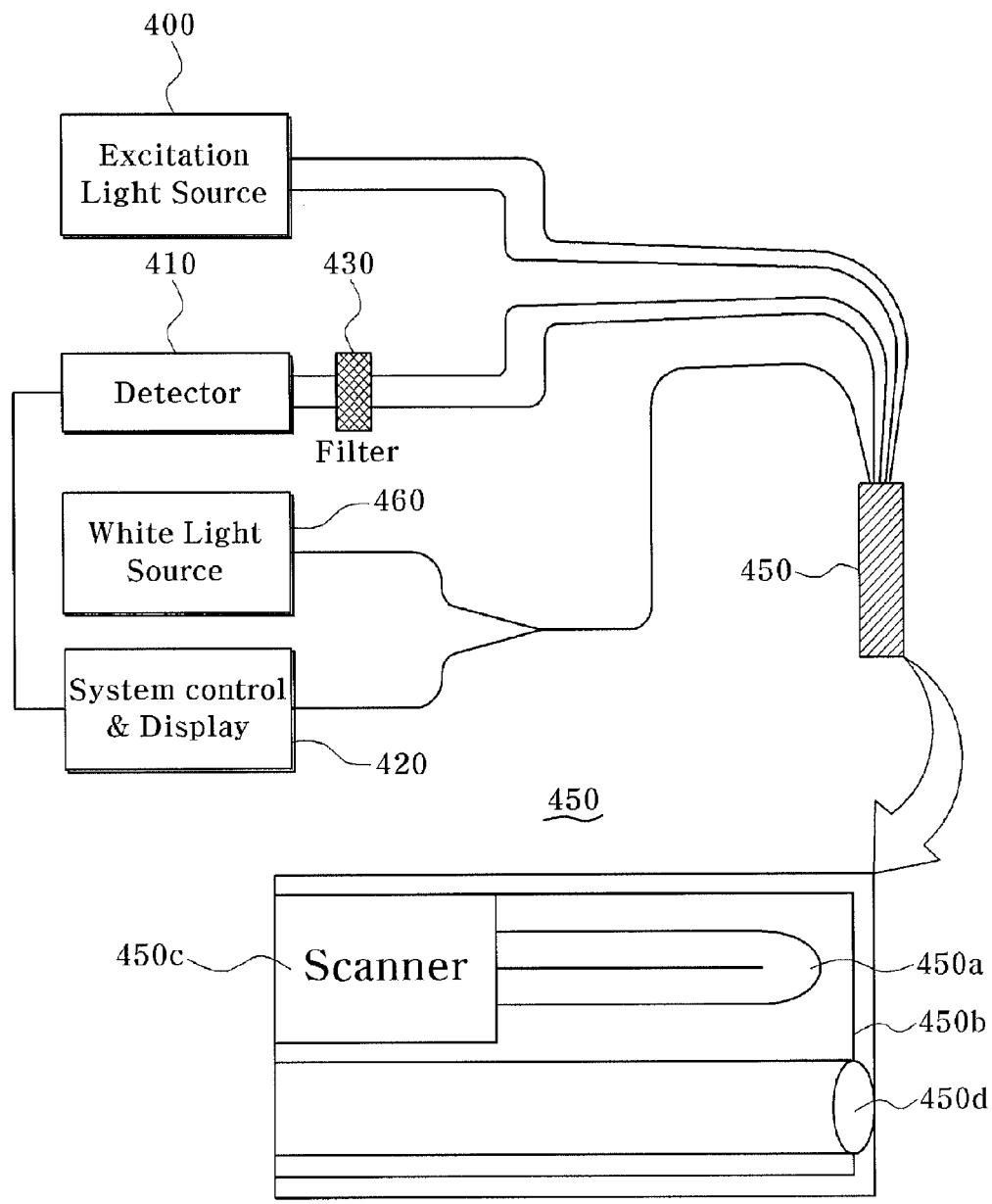
FIG. 2 is a block diagram showing an imaging system using an optical fiber array probe integrated with lenses according to an exemplary embodiment of the present invention.

FIG. 2 is a block diagram showing an imaging system using an optical fiber array probe integrated with lenses according to an exemplary embodiment of the present invention.

Referring to FIG. 2, the imaging system according to an embodiment of the present invention includes endoscope units 460, 420, and 450*d* and optical fiber array probe units 410 and 450 integrated with lenses.

The endoscope units 460, 420, and 450*d* include an endoscope probe 450*d* through which a light source 460 is transmitted to a sample, and a system control and display unit 420 including a detection unit for detecting light reflected in the endoscope probe 450*d*.

Optical fiber array probe units 410, 450*a*, and 450*c* integrated with lenses include optical fiber array probes 450*a* and 450*c* integrated with lenses including a scanner 450*c* and a detector 410. The optical fiber array probe 450*a* integrated with lenses emits the light transmitted from the light source 400 to a sample, and guides light generated from the sample.

Using the imaging system according to an embodiment of the present invention, an interior structure of a human body or a sample may be measured using the endoscope units 460, 420, and 450*d* to thereby find a position at which lesions or abnormal parts are present, and then fluorescence images or nonlinear images on the abnormal parts are immediately measured using the optical fiber array probe units 450*a*, 450*c*, and 410 to thereby analyze abnormality.

The endoscope unit is not particularly limited, and a variety of types of endoscope units may be used. For example, an electronic endoscope that includes an imaging optical system for condensing and visualizing images reflected from a sample while including an optical fiber and a lens optical system capable of transmitting and emitting white light to the sample, and a CCD, or a fiber optical endoscope that includes an optical fiber bundle and a CCD provided in a display unit may be used.

Hereinafter, the optical fiber array probe units 410, 450*a*, and 450*c* integrated with lenses will be described in detail. It is advantageous for a fluorescence spectroscopy system, a fluorescence imaging system, and a nonlinear endoscope system to be applied separately. Hereinafter, this will be described.

The optical fiber array probes 450*a* and 450*c* integrated with lenses may include an optical fiber lens that integrally connects one ends of optical fibers with each other by heating a predetermined region including one ends of two optical fiber arrays using a heating means while having a lens surface of a predetermined radius of curvature. More specifically, the optical fiber array probe unit integrated with lenses may further include a light source 400, a system control and display unit 420, and the like.

Meanwhile, the system control and display unit 420 may be configured so as to control all of the endoscope unit and the optical fiber array probe unit, and display related images, or may be separately configured.

An optical fiber that transmits light from the light source to the sample among two optical fibers of the optical fiber array probes 450a and 450b integrated with lenses is referred to as an excitation fiber, and an optical fiber that transmits light from the sample to the detector is referred to as a collection fiber.

In an excitation light source and the detector of the imaging system, it is advantageous for a fluorescence spectroscopy system, a fluorescence imaging system, and a nonlinear endoscope system to be applied separately.

As the light source 400 of the fluorescence spectroscopy system, an ultraviolet or visible light laser with a single wavelength may be used. As examples of the ultraviolet or visible light laser, a He—Ne laser, an argon-ion laser, a DPSS laser, a dye laser, a tungsten-halogen laser including a filter, a xenon lamp, an LED, and the like may be given. As a detector for the fluorescence spectroscopy system, a spectrometer is used, and in this instance, a long pass filter is used in order to measure only fluorescence signals emitted in a long wavelength compared to the excitation beam.

In addition, in the fluorescence imaging system, a light source such as a fluorescence spectroscopy system may be used, and a detector such as a long pass filter, a spectrometer, or photomultiplier tubes (PMT) may be used as the detector 410.

As the light source 400 for the nonlinear endoscope system, a light source with strong optical power for inducing nonlinear signals is required. As the light source, solid laser such as a femtosecond Ti:sapphire laser or Cr:forsterite laser, or an optical fiber femtosecond laser may be used. As the detector 410, a PMT including a band pass filter may be used in order to selectively detect light transmitted from the optical fiber array probes 450a and 450c integrated with lenses in a wavelength of a predetermined range or to detect only nonlinear signals. The excitation beam should be strongly focused in order to detect the nonlinear signals, and therefore it is preferable, when manufacturing the probe for the nonlinear endoscope, for a curvature of the lenses to be increased (larger number of openings) compared to the fluorescence spectroscopy imaging system.

An excitation beam is transmitted to an excitation fiber of the optical fiber array probes 450a and 450c integrated with lenses to thereby be focused on a sample by a lens of the end of the probe, and signals generated by the focused excitation beam are repeatedly focused on the lens to thereby be transmitted to a collection fiber. Here, the transmitted signals are passed through the filter 430, and then only signals of a desired wavelength are detected through the detector.

In this instance, the system control and display unit 420 simultaneously controls a scanner and a detector of a scanning probe, and performs a signal process on the detected signals to thereby visualize the signals. By scanning the optical fiber array probes 450a and 450c integrated with lenses, it is possible to perform optical-imaging two-dimensionally or three-dimensionally. According to another modified example of the present invention, the optical fiber array probe may not be scanned. Through this method, only point information rather than two-dimensional or three-dimensional information may be obtained.

As an example for directly driving the optical fiber array probes 450a and 450c integrated with lenses along an X axis or a Y axis, a piezoelectric translator (PZT) actuator, a micro electro mechanical system (MEMS) scanner, or a scanning method using electromagnetic force of a solenoid may be given. By driving a linear scanner in a Z-axis direction in such an XY-scanner, it is possible to perform three-dimensional imaging.

Figure 3:
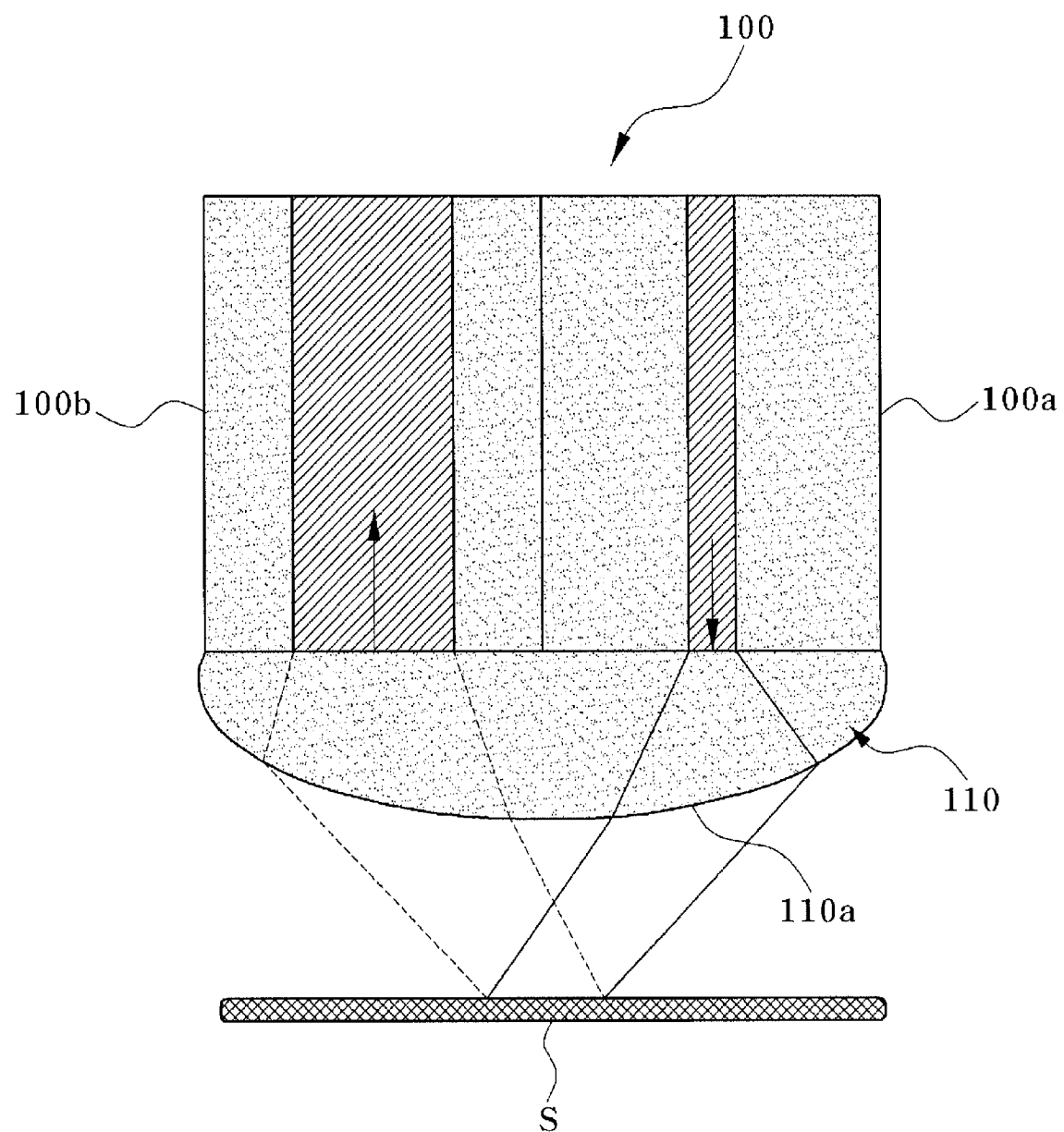
FIG. 3 is a drawing showing an optical fiber array probe that is used in an imaging system using the optical fiber array probe integrated with lenses of FIG. 2.
Figure 4:
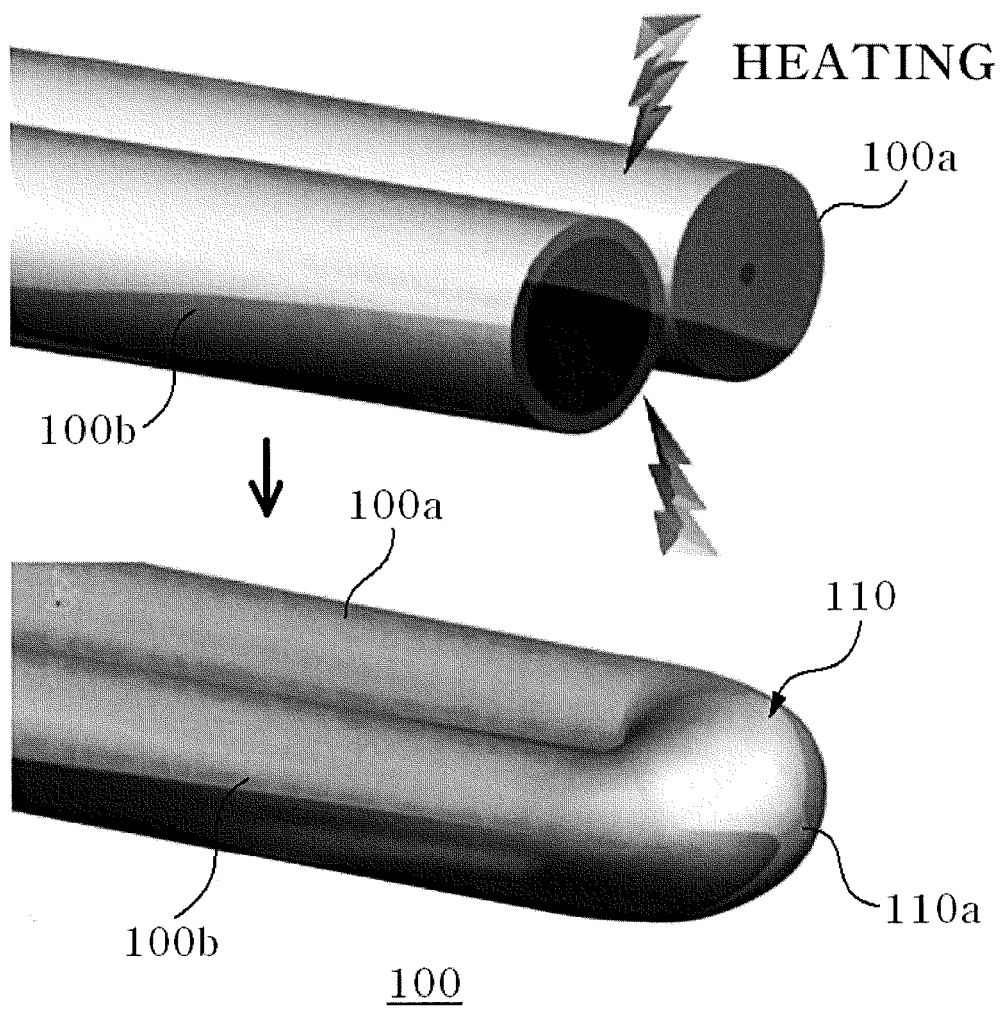
FIG. 4 is a conceptual diagram showing a method of manufacturing an optical fiber array probe used in an imaging system using the optical fiber array probe integrated with lenses of FIG. 2.

Hereinafter, the optical fiber array probes 450a and 100 of FIG. 2 will be described in detail. FIG. 3 is a drawing showing an optical fiber array probe that is used in an imaging system using the optical fiber array probe integrated with lenses, and FIG. 4 is a conceptual diagram showing a method of manufacturing an optical fiber array probe.

An optical fiber array probe 250a includes first and second optical fibers 100a and 100b, and an optical fiber lens 110. It is preferable that the first and second optical fibers 100a and 100b be arranged in parallel to each other, and one side surfaces of the first and second optical fibers 100a and 100b be arranged so as to be brought into linear contact or surface contact with each other. The first optical fiber 100a is composed of a single mode fiber (SMF) for an excitation beam, and the second optical fiber 100b is composed of a multi mode fiber (MMF) so as to receive a reflected beam (a collection beam). Here, the SMF is used for the excitation beam to reduce a size of a beam in a focal point, and the MMF is used for condensing to receive many beams due to a large core of the MMF. However, the optical fiber array probe may be manufactured using a variety of types and sizes of optical fibers other than the above-described configuration shown as an example.

The first and second optical fibers 100a and 100b may have the same or different structures, and for example, may include at least one of an SMF, an MMF, a photonic crystal fiber, and a double-cladding optical fiber.

For example, the photonic crystal fiber has a plurality of air holes around a core unlike a general SMF, and is referred to as a holey fiber or a microstructured fiber. Such a photonic crystal fiber includes a plurality of air holes (for example, 2 to 1000 air holes) regularly or irregularly arranged along a cladding of the optical fiber, and may be an optical fiber in which there are no air holes in a core of the optical fiber, or an optical fiber in which there are air holes in the core of the optical fiber, but the size thereof is different from that of air holes surrounding the core of the optical fiber.

The optical fiber lenses 110 are formed so as to be integrally connected with each other at one ends of the first and second optical fibers 100a and 100b, and include lens surfaces 100a having a predetermined radius of curvature at the ends thereof.

The optical fiber lens 110 is formed so that light wave-guided along the core of the first optical fiber 100a is expanded so as to have a sufficient size on a lens surface 110a, and the expanded light is refracted on the lens surface 110a to thereby be formed toward a center of the entire optical fiber array probe. In addition, the optical fiber lens 110 refracts a beam emitted from a sample (S) on the lens surface 110a to thereby be formed toward the second optical fiber 100b.

The optical fiber lenses 110 configured as above may be integrally formed at one ends of the first and second optical fibers 100a and 100b using a method of heating at a high temperature using arc-discharge, a laser, or the like.

An operation principle of the optical fiber array probe 100 integrated with lenses according to an embodiment of the present invention which has been described as above will be described herein. Light generated by an external light source unit is transmitted through a core of the first optical fiber 100a that is an SMF, the beam transmitted through the core of the first optical fiber 100a is expanded in the optical fiber lens 110, and the expanded beam is refracted on the lens surface 110a formed at the end of the optical fiber lens 110 to thereby be oriented to a center of the entire optical fiber array probe. In this instance, the beam emitted from the sample (S) is transmitted through a core of the second optical fiber 110b that is an MMF, using the optical fiber lens 110.

Meanwhile, according to an embodiment of the present invention, the optical fiber array probe is implemented using two strands of first and second optical fibers 100a and 100b, but the present invention is not limited thereto. For example, at least two strands of optical fibers may be implemented which are brought into contact with each other.

The above-described optical fiber array probe integrated with lenses and the manufacturing method thereof according to preferred embodiments of the present invention have been described, but the present invention is not limited thereto.

As described above, according to the embodiments of the present invention, an endoscope system and an optical fiber array probe system may be integrally manufactured, thereby simultaneously obtaining structural information and functional information of a sample.

In addition, according to the embodiments of the present invention, when an abnormality is detected using an endoscope while examining interior parts of a human body, fluorescence signals or nonlinear signals of abnormal parts may be immediately checked using an optical fiber array probe system.

In addition, according to the embodiments of the present invention, strong optical coupling efficiency may be obtained in a focal distance using an optical fiber array probe integrated with lenses, thereby improving signal measuring efficiency and controlling a curvature of the lenses. Therefore, the present invention may be utilized as a fluorescence probe that enables depth decomposition capable of measuring fluorescence measurement signals in a specific depth or a probe for detecting nonlinear signals requiring connection of a strong excitation beam. In addition, a lens is directly formed at the end of the optical fiber to thereby have a significantly compact size, and a working distance is obtained due to the lens to thereby manufacture a probe capable of being scanned, and therefore a fluorescence or nonlinear imaging system may be implemented using the probe.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. An optical fiber array probe imaging system integrated with an endoscope, comprising:
   an endoscope unit; and
   an optical fiber array probe unit integrated with lenses,
   wherein the endoscope unit includes a light source, an endoscope probe through which the light source is transmitted to a sample, and a detection unit for detecting light reflected in the endoscope probe, and
   wherein the optical fiber array probe unit integrated with lenses includes
   an optical fiber array probe integrated with lenses including an optical fiber lens with a lens surface of a predetermined radius of curvature in which one ends of optical fibers are integrally connected with each other by heating a predetermined region including the one ends of two of the optical fibers using a heating means, as an optical fiber array probe integrated lens on which the light transmitted from the light source is incident and which guides light reflected from the sample, and
   a detector for selectively detecting the light transmitted from the optical fiber array probe integrated with lenses in a predetermined range of wavelength.

2. The optical fiber array probe imaging system integrated with the endoscope of claim 1, wherein the detector includes a filter for allowing a wavelength to be selectively passed.

3. The optical fiber array probe imaging system integrated with the endoscope of claim 1, wherein a system control and display unit for controlling the system and displaying the detected light is connected to the detector.

4. The optical fiber array probe imaging system integrated with the endoscope of claim 1, wherein the optical fiber array probe integrated with lenses is configured so as to be two-dimensionally or three-dimensionally scanned.

5. The optical fiber array probe imaging system integrated with the endoscope of claim 1, wherein the imaging system is manufactured as a fluorescence spectroscopy system, a fluorescence imaging system, or a system for measuring and analyzing nonlinear images.

* * * * *